US010438436B2

(12) United States Patent
Eastham et al.

(10) Patent No.: US 10,438,436 B2
(45) Date of Patent: Oct. 8, 2019

(54) METHOD AND SYSTEM FOR DETECTING STAINING

(71) Applicant: SPINNAKER INTERNATIONAL LIMITED, Saltash Cornwall (GB)

(72) Inventors: Paul Eastham, Saltash (GB); Nick Tripp, Saltash (GB); Tony Westington, Saltash (GB); Phil Culverhouse, Plymouth (GB)

(73) Assignee: SPINNAKER INTERNATIONAL LIMITED, Saltash Cornwal (GB)

(*) Notice: Subject to any disclaimer, the term of this patent is extended or adjusted under 35 U.S.C. 154(b) by 80 days.

(21) Appl. No.: 15/760,408

(22) PCT Filed: Aug. 26, 2016

(86) PCT No.: PCT/GB2016/052663
§ 371 (c)(1),
(2) Date: Mar. 15, 2018

(87) PCT Pub. No.: WO2017/046561
PCT Pub. Date: Mar. 23, 2017

(65) Prior Publication Data
US 2019/0057568 A1    Feb. 21, 2019

(30) Foreign Application Priority Data
Sep. 17, 2015  (GB) .................................. 1516490.8

(51) Int. Cl.
*G06K 9/00* (2006.01)
*G07D 7/20* (2016.01)
(Continued)

(52) U.S. Cl.
CPC ....... *G07D 7/2016* (2013.01); *G01N 21/8851* (2013.01); *G07D 7/187* (2013.01);
(Continued)

(58) Field of Classification Search
CPC .................................................... G07D 7/2016
See application file for complete search history.

(56) References Cited

U.S. PATENT DOCUMENTS

| 2004/0238619 A1 | 12/2004 | Nagasaka |
| 2007/0053573 A1 | 3/2007 | Rabinovich |
| 2011/0019881 A1 | 1/2011 | Natori |

FOREIGN PATENT DOCUMENTS

| EP | 2187359 | 5/2010 |
| EP | 2645339 | 10/2013 |

(Continued)

OTHER PUBLICATIONS

Search Report issued in Application No. GB1516490.58 dated Mar. 18, 2016.

(Continued)

*Primary Examiner* — Stephen P Coleman
(74) *Attorney, Agent, or Firm* — Knobbe, Martens, Olson & Bear, LLP

(57) ABSTRACT

A method for detecting staining on a media item, the method comprising: capturing (22) a digital image of the media item, the digital image comprising a plurality of pixels representing color information of the media item; comparing (30) the captured digital image to a reference image, wherein comparing the captured digital image to the reference image comprises: generating a histogram for each of a plurality of kernel patches of the captured digital image, wherein each of the plurality of kernel patches of the captured digital image covers an area of the captured digital image, such that the entire captured digital image is covered by the plurality of kernel patches; comparing (40) the histogram for each of the plurality of kernel patches of the captured digital image to a histogram of a corresponding kernel patch of the reference image to generate a distance metric; and based on the (Continued)

generated distance metrics, determining if staining is present on the media item.

24 Claims, 8 Drawing Sheets

(51) Int. Cl.
  *G07D 7/187* (2016.01)
  *G07D 7/206* (2016.01)
  *G01N 21/88* (2006.01)
(52) U.S. Cl.
  CPC ........... *G07D 7/206* (2017.05); *G07D 7/2008* (2013.01); *G01N 2021/8887* (2013.01)

(56) References Cited

FOREIGN PATENT DOCUMENTS

| | | |
|---|---|---|
| GB | 2 431 793 | 5/2007 |
| JP | 2015026229 | 2/2015 |
| WO | WO 99/60353 | 11/1999 |

OTHER PUBLICATIONS

International Search Report in Application No. PCT/GB2016/052663 dated Nov. 7, 2016.

METHOD AND SYSTEM FOR DETECTING STAINING

CROSS REFERENCE TO RELATED APPLICATIONS

The present application is a national stage application of International Patent Application No. PCT/GB2016/052663, filed on Aug. 26, 2016, which claims priority to Great Britain Provisional Application No. 1516490.8, filed Sep. 17, 2015.

TECHNICAL FIELD

The present application relates to the field of stain detection, in particular detection of staining or other marking of items such as bank notes with security ink or dye products.

BACKGROUND TO THE INVENTION

Automated payment machines are commonplace, in applications ranging from soft drinks vending to high stakes gambling. Such machines must be capable of reliably authenticating notes and coins in a range of conditions with no human interaction.

To deter would-be thieves of bank notes in transit, it has become commonplace for notes to be stored and transported in secure containers which release an indelible dye or ink onto the bank notes in the event that the security container is stolen or otherwise interfered with, to mark and stain the bank notes, thus rendering them worthless and unusable. It is usually not possible to clean bank notes which have been marked in this way without damaging their original printing.

In addition to banknotes being purposely stained, it is possible for notes to become marked or degraded accidentally through spillage, general wear and graffiti.

Certain currency issuing authorities have mandated that security stained notes deemed unfit for circulation are neither accepted in a transaction nor returned to the customer, but are instead retained so as to be removed from circulation. This is easy to achieve in transactions involving a human cashier, where the cashier can physically inspect the note, but is more difficult to achieve with the certainty necessary when bank notes are used in automated payment machines.

Although automated payment machines typically include note validators which use a comprehensive suite of tests to determine the authenticity of a bank note, few have the ability reliably to detect notes that have been degraded specifically by staining ink. As a result a growing problem is the use of automated payment machines to convert large quantities of stained notes into clean notes that can then be used with impunity.

Current note validator systems may include visible, ultraviolet and infrared imaging devices as well as magnetic and capacitance sensing technologies to validate banknotes and also detect stains. However, existing techniques are often unable to determine the nature of the stain or accurately compute the affected area. To improve reliability additional additives such as those with infrared absorption characteristics can be added to the staining ink to improve machine detection. These additives however significantly increase the price of the inks.

Accordingly, it would be desirable to provide a system that can reliably determine the extent of staining on a bank note and whether such staining is likely due to security staining inks.

SUMMARY OF INVENTION

According to a first aspect of the present invention there is provided a method for detecting staining on a media item, the method comprising: capturing a digital image of the media item, the digital image comprising a plurality of pixels representing colour information of the media item; comparing the captured digital image to a reference image, wherein comparing the captured digital image to the reference image comprises: generating a histogram for each of a plurality of kernel patches of the captured digital image, wherein each of the plurality of kernel patches of the captured digital image covers an area of the captured digital image, such that the entire captured digital image is covered by the plurality of kernel patches; comparing the histogram for each of the plurality of kernel patches of the captured digital image to a histogram of a corresponding kernel patch of the reference image to generate a distance metric; and based on the generated distance metrics, determining if staining is present on the media item.

The method of the present invention facilitates the detection and quantification of staining on media items such as bank notes, and the identification of such staining as being due to security staining inks or dyes. The method may be used in automated payment machines and the like to detect security stained bank notes, to facilitate the retention and removal from circulation of such stained bank notes, thereby making it more difficult for such notes to be used or exchanged for clean currency. This in turn reduces the incentive for thieves to attempt to steal bank notes from ATMs or other cash handling machines, or to attempt to steal bank notes in transit.

The method may further comprise determining the nature of detected staining based on the generated distance metrics.

For example, determining the nature of the detected staining may comprise, for each kernel patch of the captured digital image: generating a dye certainty metric for the kernel patch; and combining the generated dye certainty metric with the generated distance metric for the kernel patch to generate a kernel probability score which is representative of the likelihood that the detected staining is due to a staining dye.

The dye certainty metric may be weighted by a hue certainty metric.

The hue certainty metric may depend upon saturation and intensity values of the kernel patch.

The dye certainty metric may be weighted by a dye hue similarity metric.

The dye hue similarity metric may be generated by comparing a hue value of the kernel patch of the captured digital image with a hue value of a known staining dye.

The dye certainty metric may be weighted by an intensity difference metric.

The intensity difference metric may be generated by comparing an intensity value of the kernel patch of the captured digital image with an intensity value of a corresponding kernel patch of the reference image.

Generated distance metric may be a Chi Square distance between the histogram of the kernel of the captured digital image and the histogram of the corresponding kernel of the reference image.

The dye hue similarity metric may be generated by performing a colour de-blending process using colour values of the kernel of the captured digital image and the corresponding kernel of the reference image.

The colour de-blending process may comprise: generating, from the colour values of the kernel of the captured digital image and the corresponding kernel of the reference image, respective captured and reference colour spectra; dividing the reference colour spectrum by the captured colour spectrum to generate an addition colour spectrum; converting the addition colour spectrum to an RGB triplet; and comparing the RGB triplet to a known dye to generate the dye hue similarity metric.

The method may further comprise, for each individual kernel patch of the plurality of kernel patches of the captured digital image: identifying kernel patches neighbouring the individual kernel patch; examining each neighbouring kernel patch to assess whether that neighbouring kernel patch is deemed to be stained; if a neighbouring kernel patch is deemed to be stained, increasing a kernel probability score of the individual kernel patch; quantifying the extent of staining by comparing the number of individual kernel patches of the captured digital image that have a kernel probability score that meets a threshold.

The method may further comprise: if no neighbouring kernel patch is deemed to be stained, decreasing a kernel probability score of the individual kernel.

Pixels of the kernels may be weighted such that pixels positioned towards a centre of the kernel have higher weights than pixels positioned towards edges of the kernel.

For example, the pixels of the kernels may be weighted according to a two-dimensional spatial Gaussian distribution.

Pixels of the kernels may be weighted according to a Gaussian distribution applied over a colour distance of the pixels and histogram intervals to which the pixels are to be added.

Each of the plurality of kernel patches may overlap a neighbouring kernel patch.

The method may further comprise applying a transformation to the captured digital image to align and resize the captured digital image to correspond in size and orientation to the reference image Capturing the digital image of the media item may comprise capturing a digital image of one or both sides of the media item.

The media item may be a bank note.

The reference image may be retrieved from a database containing a plurality of reference images.

According to a second aspect of the invention there is provided a system for detecting staining on a media item, the system comprising: an imaging device for generating digital image of the media item, the digital image comprising a plurality of pixels representing colour information of the media item; and a processor, the processor being configured to perform the method of any one of the preceding claims.

The system may further comprise a camera for capturing an image of a user of the system, and the processor may be configured to actuate the camera to capture an image of the user if the total extent of staining on the media item meets a threshold.

BRIEF DESCRIPTION OF THE DRAWINGS

Embodiments of the invention will now be described, strictly by way of example only, with reference to the accompanying drawings, of which.

DESCRIPTION OF THE EMBODIMENTS

Figure 1:
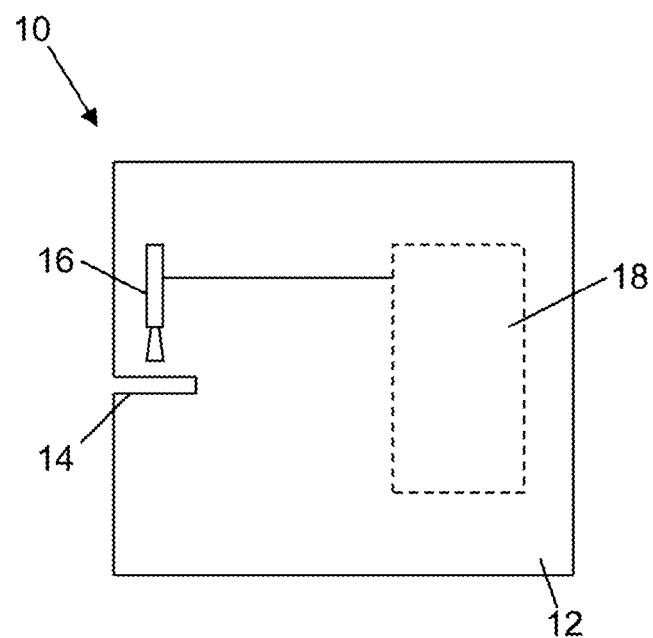
FIG. 1 is a schematic representation of an automated payment machine.

FIG. 1 is a schematic representation of an automated payment machine incorporating an exemplary detection system for detecting staining of bank notes. The automated payment machine is shown generally at 10, and comprises a housing 12 within which is provided a slot 14 for receiving bank notes. The housing 12 also contains a detector arrangement including an imaging device 16 such as a CCD (charged couple device) based camera. The imaging device 16 is capable of capturing an image of a bank note that is introduced to the machine 10 through the slot 12. The imaging device 16 may be sensitive to the infra-red and ultra-violet ranges of the electromagnetic spectrum, as well as the visible range.

The imaging device 16 is connected to a processing system 18, which receives information from the imaging device 16, and, based on the received information, makes a decision as to whether the introduced bank note is valid of not. The processing system 18 may be configured to prompt the automated payment machine 10 to reject or retain a bank note that has been introduced through the slot 14, if the processing system 18 determines that the bank note is not valid, for example if the processing system 18 determines that the bank not is not genuine, or that the degree of staining or other degradation of the bank note meets a predefined threshold.

Figure 2:
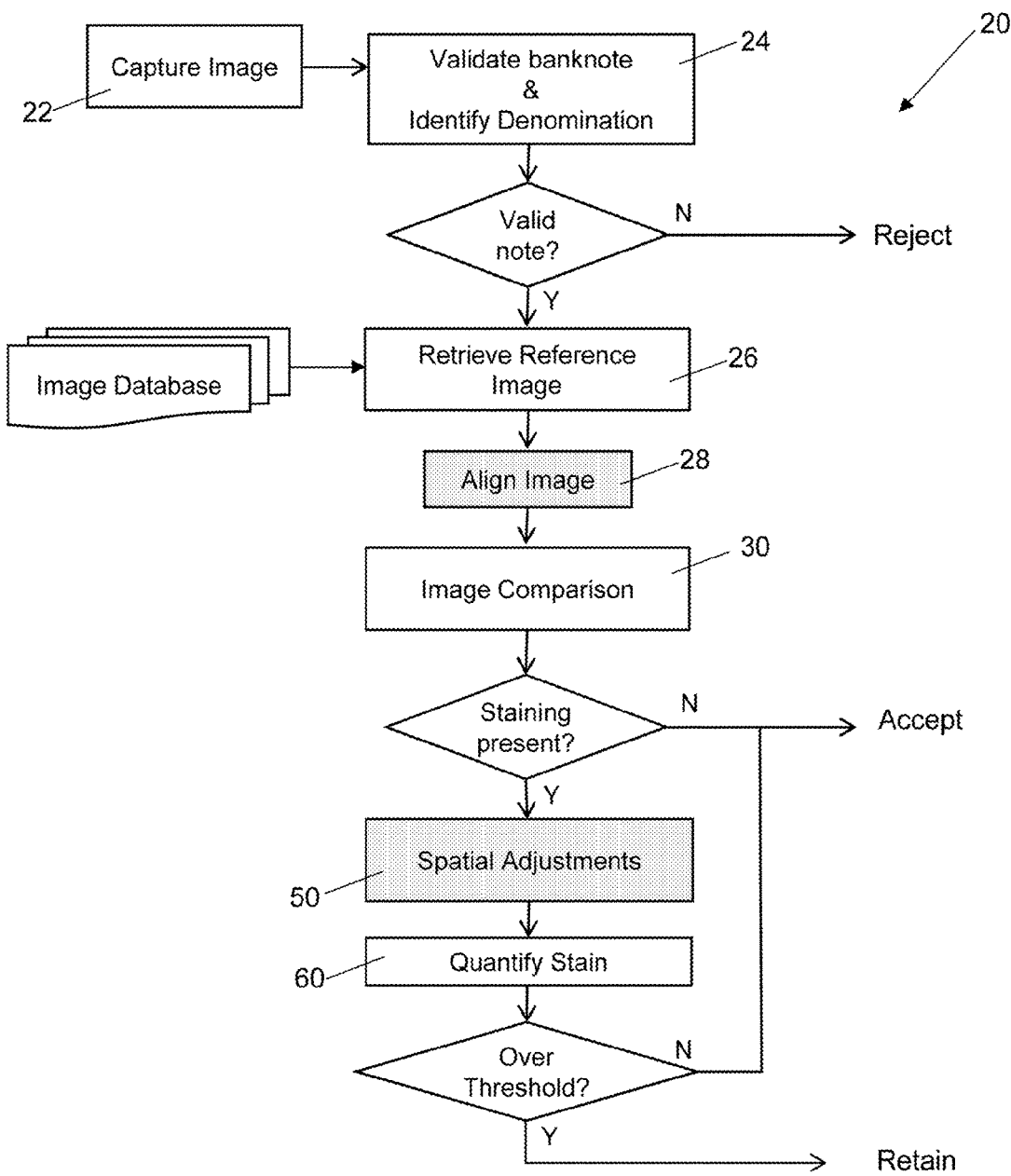
FIG. 2 is a is a flow diagram illustrating a process performed to determine a degree of staining of a bank note.

FIG. 2 is a flow diagram illustrating a process 20 performed by the processing system 18 in determining a degree of staining of a bank note.

Once a bank note or other media item has been introduced into the payment machine 10, the imaging device 16 captures a digital image of the bank note at step 22, this digital image comprising a plurality of pixels representing colour information of the media item. This capture process may generate an image of one or both sides of the media item. The image(s) may contain additional information that is used in a subsequent process of validating the introduced media item (described below), but is not relevant for the process of determining the extent and nature of staining of the media item. The capture process may also capture additional information that may be used in the subsequent process of identifying and quantifying staining of the media item, such as the reflectance of the media item over different wavelengths.

At step 24 the captured image of the introduced media item is processed by the processing system 18 for the purpose of validation, i.e. to determine whether the media item that has been introduced into the payment machine 10 is a valid bank note. Assuming that the media item is validated as a valid bank note, the denomination of the introduced bank note is determined by the processing system 18. Techniques for validating the bank note and determining its denomination will be familiar to those skilled in the art and thus will not be described in detail here. If the note is deemed not to be valid it is rejected, causing the processing system 18 to prompt the payment machine to eject the bank note. Otherwise the process 20 continues.

Once the introduced media item has been validated as a bank note and the denomination of the bank note has been determined, a reference image of a corresponding clean (i.e. unstained and undegraded) bank note of the same denomination is retrieved from a database containing a plurality of reference images of clean bank notes. This database is preferably stored locally, for example on a hard drive or non-volatile memory of the processing system 18. Alternatively, to facilitate updating of the database of reference images, the database may be held on a central server that can be accessed by the processing system 18, for example through a wired or wireless network connection.

If required, an additional step 28 may be performed to apply a transformation to the captured digital image to align and resize the captured digital image so that it corresponds in size and orientation to the retrieved reference image.

At stage 30 a kernel based image comparison process is performed to determine if staining is present on the introduced note. This process will be described in more detail below, with reference to FIG. 3. If this process determines that no staining is present, the note is accepted, and the processing system 18 causes the payment machine 10 to retain the note and provide the requested goods or services.

Figure 8:
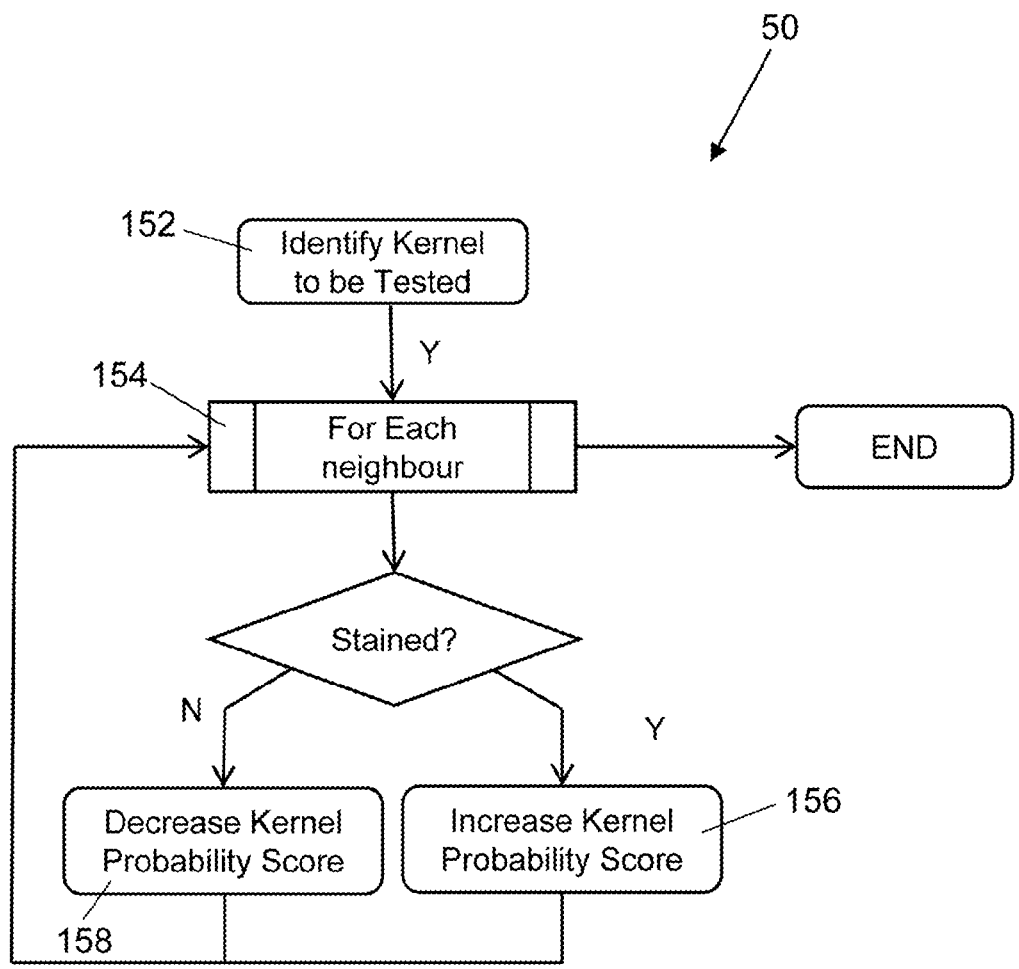
FIG. 8 is a flow diagram illustrating steps of a process in which global spatial information of a stain is used to increase the accuracy with which the area of staining detected is calculated.

If the image comparison process performed at step 30 determines that staining is present, a further stage 50 may be performed, in which global spatial information of the stain is used to increase the accuracy with which the area of staining detected is calculated, as will be described below with reference to FIG. 8. This helps to improve the accuracy of a final decision step 60, in which the extent of the staining is quantified and compared to a predetermined threshold. If the extent of the staining meets the threshold a decision is made to retain the introduced note without providing the requested goods or services, and so the processing system 18 causes the payment machine 10 to retain the note without providing the requested goods or services. On the other hand, if the extent of the staining does not meet the threshold the note is accepted, and the processing system 18 causes the payment machine 10 to retain the note and provide the requested goods or services.

The kernel based image comparison process performed at step 30 involves moving a kernel, which is a predefined and pre-weighted matrix, over the captured digital image of the introduced note in such a way that each kernel "patch" (i.e. the area of the captured digital image that is currently covered by the kernel) overlaps its adjacent or neighbouring kernel patches, until the entire captured digital image of the introduced note has been covered. A histogram for each kernel patch of the captured digital image is generated as the kernel moves over the captured digital image.

At the same time, an identical kernel is moved over the reference image in the same manner, and a histogram for each kernel patch of the reference image is generated as the kernel moves over the reference image. The histogram generated for each kernel patch of the captured digital image is compared to the histogram generated for the corresponding kernel patch of the reference image to generate a difference value, which is used by the processing system 18 to determine a probability that staining is present on the introduced note.

The process 30 will now be described in more detail with reference to FIG. 3, which is a flow diagram showing the steps of the process 30, and FIG. 4, which diagrammatically illustrates the process of moving a kernel over the captured digital image of the introduced note.

Figure 4:
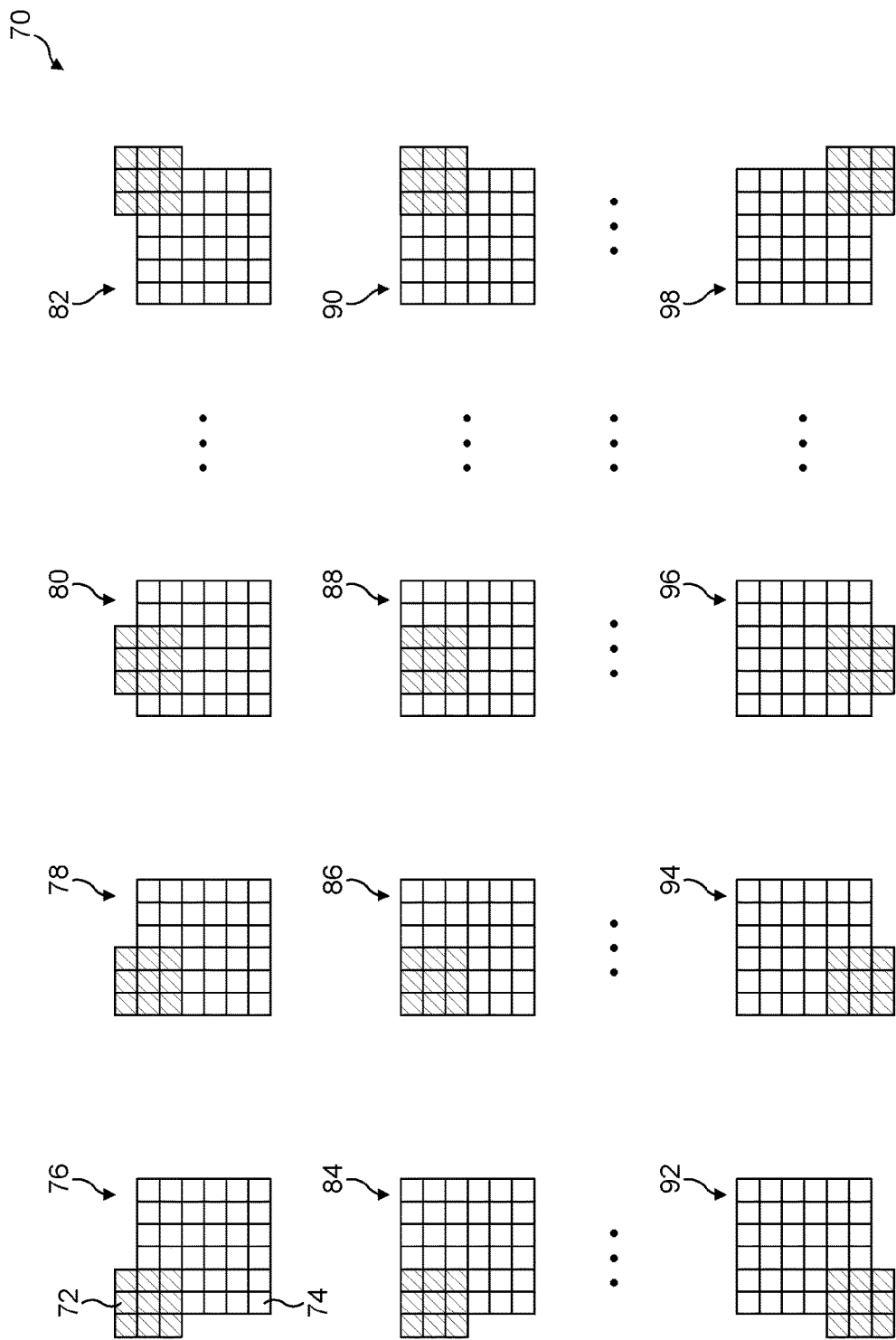
FIG. 4 is a schematic representation of a process of moving a kernel over a captured digital image.

As indicated above, the kernel is a predefined and pre-weighted matrix, and is represented in FIG. 4 as a 3×3 pixel grid 72 which is moved over the captured digital image of the introduced note, which is represented in FIG. 4 by a 6×6 pixel grid 74. It will of course be appreciated that the grids 72, 74 in FIG. 4 are for illustrative purposes only; in a real-world implementation of the process 30 both the captured digital image 74 and the kernel 72 will be significantly larger.

Figure 5:
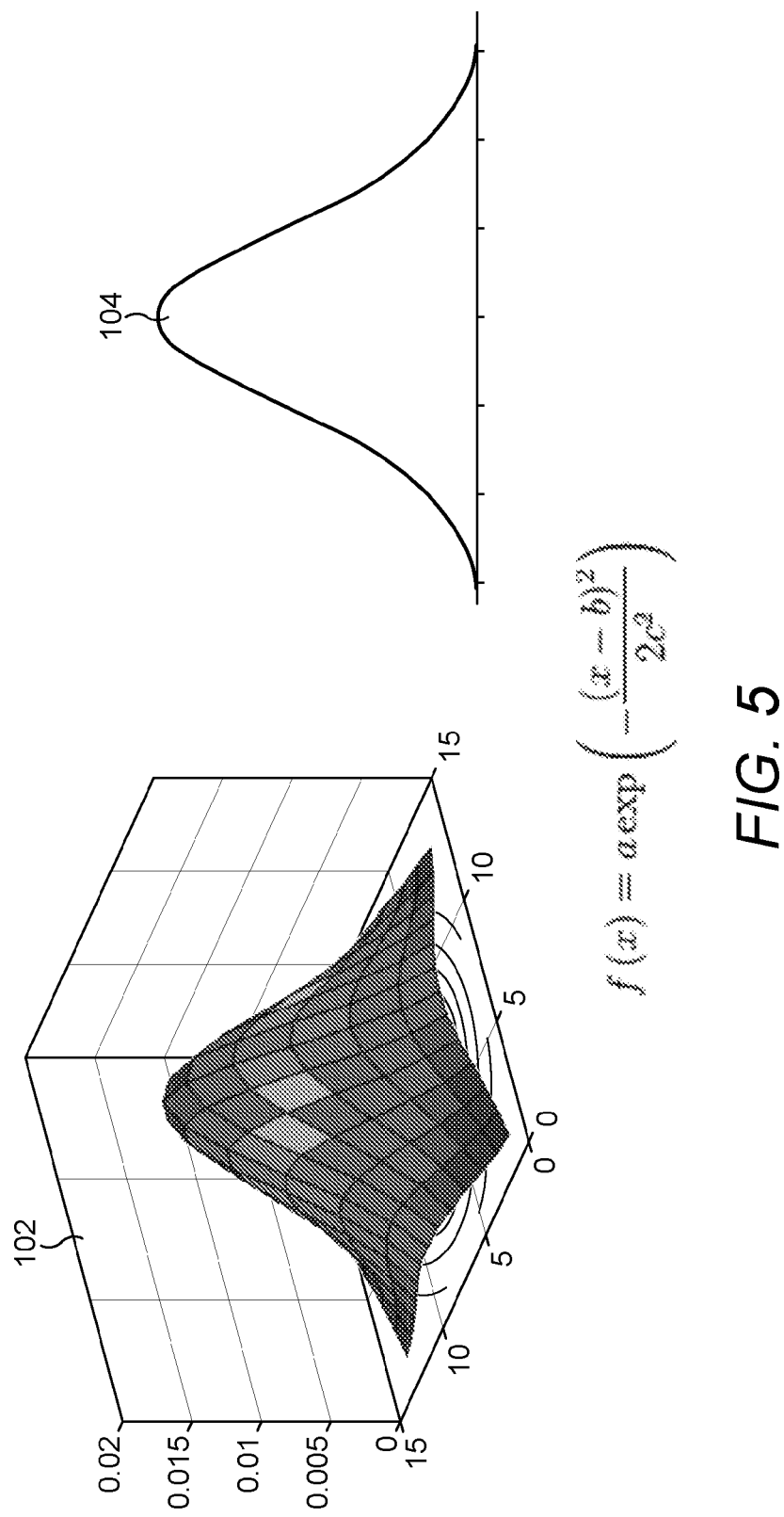
FIG. 5 is a schematic representation of Gaussian distributions that may be used in generating histograms for kernel patches.

The kernel 72 is locally weighted in terms of distance to the centre of the kernel; pixels positioned towards the centre of the kernel have higher weights than those positioned towards the edges of the kernel. For example, the contribution of the pixels may be weighted according to a two-dimensional spatial Gaussian kernel of the type shown at 102 in FIG. 5. The contributions of the pixels of the kernel 72 may additionally be weighted according to a further Gaussian kernel of the type shown at 104 in FIG. 5 applied over the colour distance of the pixel values and the histogram intervals (bins) to which the pixels are to be added, to provide smoothing over the spatial and colour values of the pixels.

Figure 3:
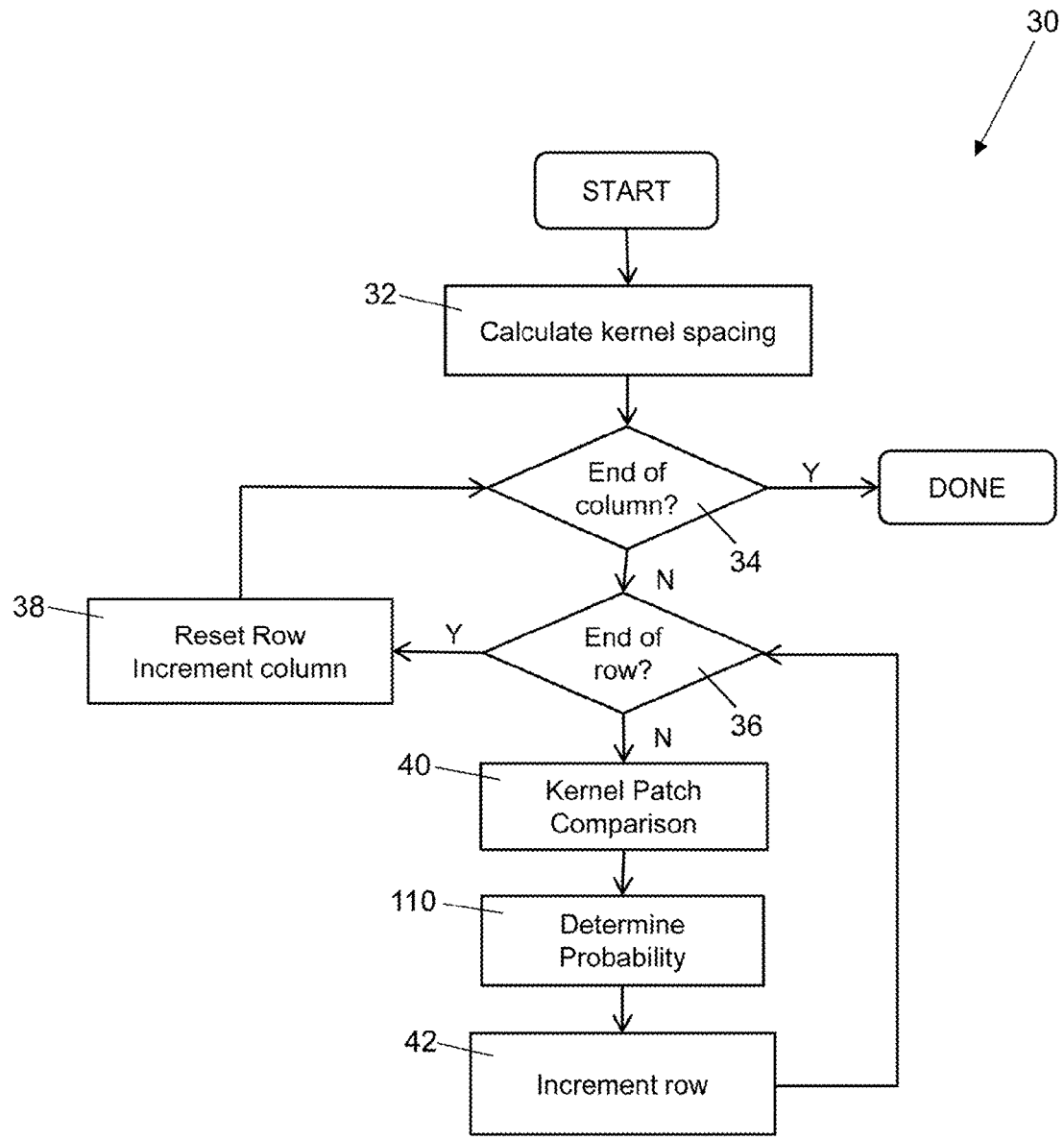
FIG. 3 is a flow diagram showing steps of a kernel based image comparison process.

Returning to the flow chart of FIG. 3, a first step 32 in the process 30 is to calculate a kernel spacing. This step calculates the correct kernel step distance and overlap between neighbouring or adjacent kernel patches, and ensures that the kernel transitions correctly between pixel rows and columns in the captured digital image and the reference image, without the need to resize the images to accommodate a particular number of kernel steps. This is achieved by allowing the overlap distances along an entire row or column to accommodate any variation from the best-fitting integer number of kernel patches required to cover the image in relation to the image size.

At the start of the process 30, the kernel is positioned with the overlap distance for both rows and columns of pixels lying outside of the image, as shown at 76 in FIG. 4, in which the left-most three pixels of the kernel 72 lie to the left of the image 74, and the top-most three pixels of the kernel 72 lie above the image 74. A kernel patch comparison is then performed (step 40 of FIG. 3), between the kernel patch of the captured digital image and the corresponding kernel patch of the reference image.

The kernel patch comparison 40 involves generating a histogram such as a two-dimensional hue/lightness histogram for the current kernel patch of the captured digital image and the corresponding kernel patch of the reference image. This 2D hue/lightness histogram is generated using two pre-calculated Gaussian weightings. The first of these weightings is a 2D planar Gaussian distribution of the type shown at 102 in FIG. 5, in which pixels closer to the centre of the kernel contribute more to the output than those at the edge. This weighting is used to smooth the spatial information in the histogram. The second weighting is a Gaussian distribution of the type shown at 104 in FIG. 5, which weights the value of the pixels such that the closer the colour value of a pixel is to a histogram interval, the more is added to that interval. This helps to prevent sudden changes in the histogram if the colour value of a pixel crosses interval borders. Both of these Gaussian distributions are pre-calculated and stored in the processing system 18 (e.g. in a hard drive or non-volatile memory of or associated with the processing system 18), to improve efficiency. The 2D spatial Gaussian distribution 102 is calculated based on the size of the kernel, whilst the histogram Gaussian distribution 104 is calculated based on the number of intervals used in the histogram.

Once the histograms have been generated for each of the captured digital image and the reference image, the Chi Square distance between the kernel patch of the captured digital image and the corresponding kernel patch of the reference image is calculated according to the equation:

$$d(H_1, H_2) = \sum_I \frac{(H_1(I) - H_2(I))^2}{H_1(I)},$$

where $H_1$ is the histogram for the captured digital image, $H_2$ is the histogram for the reference image, and I is the number of intervals (bins) in the histograms.

The Chi Square distance is a measure of the difference between the respective histograms and therefore can be used to indicate whether there is any ink staining on the introduced note, and to quantify the extent of the staining.

Once the Chi Square distance has been calculated for the first kernel patch, a row count is incremented by the kernel size minus the desired overlap (step 42 of FIG. 3), and the kernel moves to the left by a corresponding distance to the next kernel patch along. A further kernel patch comparison 40 is then performed as described above, and the row count is again incremented.

At each step, a determination is made as to whether the kernel has reached the end of the last column of pixels of the image. If so, the process 30 ends, because the kernel has moved over the entire image. If not the process 30 moves to step 36, in which a determination is made as to whether the kernel has reached the end of the current row of pixels.

If it is determined that the kernel has reached the end of the current row of pixels, the process 30 moves to step 38, in which the row count is reset to zero and a column count is incremented by the kernel size minus the desired overlap, and the kernel moves downward by a corresponding distance to the next kernel patch down.

In this way, the kernel moves over the image in row/column fashion from top left to bottom right, as illustrated in stages 76-98 in FIG. 4. At each stage, a further kernel patch comparison 40, as described above, is performed between the kernel patch of the captured digital image and the corresponding kernel patch of the reference image, to generate a Chi Square distance between the histograms of the kernel patch of the captured digital image and the corresponding kernel patch of the reference image.

As indicated above, the Chi Square distance is a measure of the difference between the respective histograms and therefore can be used to indicate whether there is any ink staining on the introduced note; a high Chi Square distance indicates a large difference between the kernel patch of the captured digital image and the corresponding kernel patch of the reference image. Thus, the Chi Square distance for each kernel patch pair (i.e. the kernel patch of the captured digital image and the corresponding kernel patch of the reference image) may be used directly to determine whether the extent of staining of the introduced note is sufficient to warrant the note being retained by the payment machine 10 without providing the requested goods or services, so as to remove the introduced note from circulation.

Thus, the Chi Square distance for each kernel patch pair may be compared to a threshold to generate a staining score, which may be for example a binary (yes/no or 1/0) value, for each kernel patch of the captured digital image. The staining scores for all of the kernel patches may then be combined to generate an overall staining score for the entire captured digital image, and this overall staining score may be compared to a threshold to determine whether the introduced note will be deemed stained or not. If the overall staining score meets the threshold, the introduced note may be deemed to be stained, causing a decision to be made to retain the introduced note without providing the requested goods or services. In this case the processing system 18 causes the payment machine 10 to retain the note without providing the requested goods or services. On the other hand, if the overall staining score does not meet the threshold the note may be deemed not to be stained and therefore to be acceptable. In this case the processing system 18 causes the payment machine 10 to retain the note and provide the requested goods or services.

Figure 6:
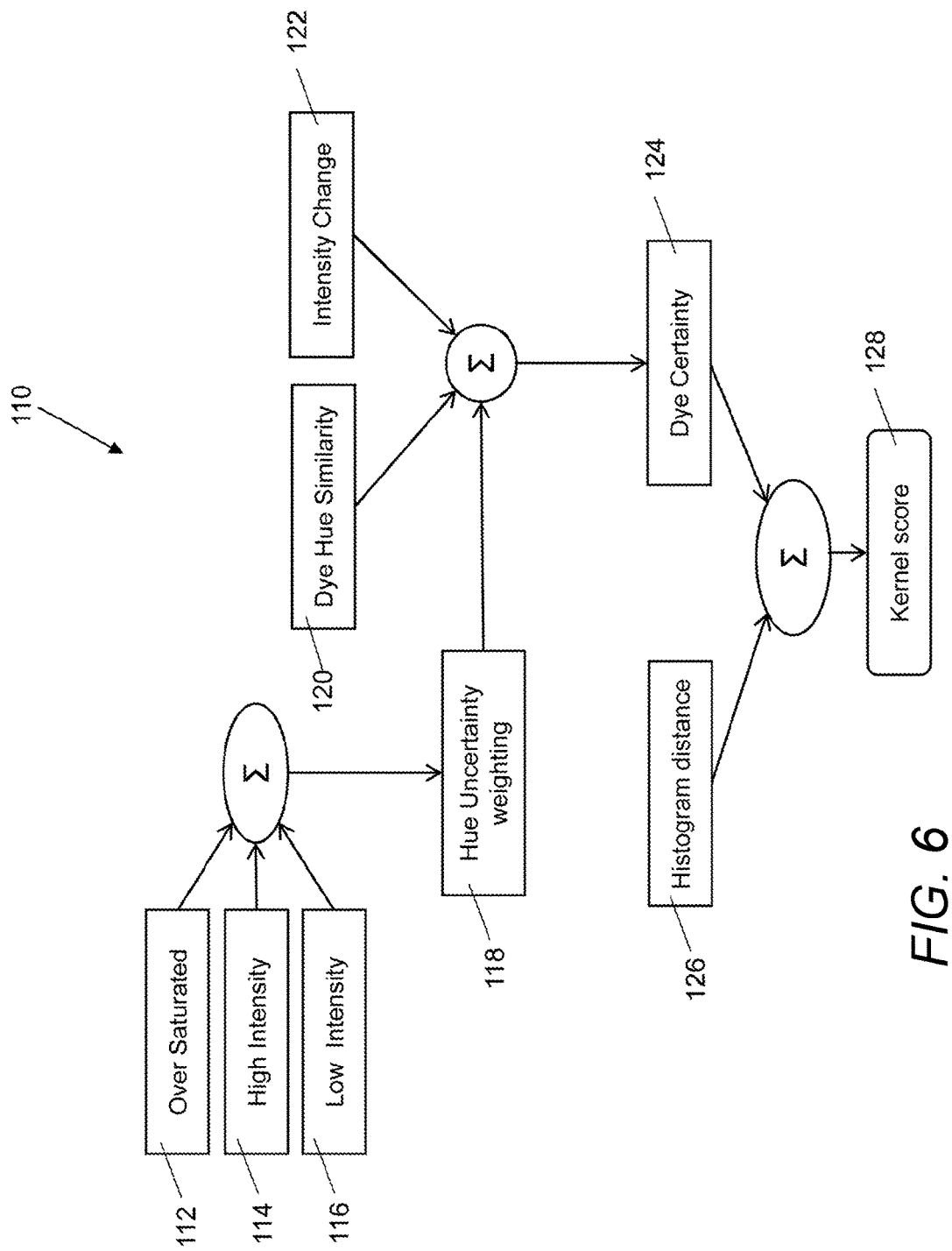
FIG. 6 is a schematic representation of fuzzy rules used by a probabilistic fuzzy logic system that may be used to determine the nature of a stain.

The Chi Square distances calculated in the kernel patch comparison steps can also be input, at step 110, to a probabilistic fuzzy logic system which uses the calculated Chi Square distance and other information such as colour information to determine the nature of the stain, as will now be described with reference to FIG. 6, which is a schematic diagram illustrating the fuzzy rules applied in step 110.

Prior to any fuzzy logic being applied, the colour data of the pixels of the captured digital image must be converted into probabilities. A hue certainty metric is derived to determine the reliability of the hue value of each kernel patch. This hue certainty metric depends upon several criteria. For example, if the saturation of the kernel patch is approaching grey, the hue certainty value is reduced. If the lightness (intensity) of the kernel patch is approaching white or is approaching black, the hue certainty value is reduced. Thus, the properties "over saturated" 112, "high intensity" 114 and "low intensity" 116 are added to generate the hue certainty metric 118.

The hue certainty metric 118 is used as a weighting to a probabilistic dye match metric 124. A dye hue similarity metric 120, which represents the level of similarity in hue between a kernel patch of the captured digital image and a known dye used for staining bank notes, and an intensity difference metric 122, which represents the level of similarity in intensity between a kernel patch of the captured digital image and a corresponding kernel patch of the reference image, are combined with the hue certainty metric 118 to generate the dye certainty metric 124.

The dye certainty metric 124 for a particular kernel patch is combined with the Chi Square distance 126 previously calculated for that kernel patch to generate an overall kernel probability score, which is representative of the likelihood that the staining on the introduced note is due to a staining dye.

Figure 7:
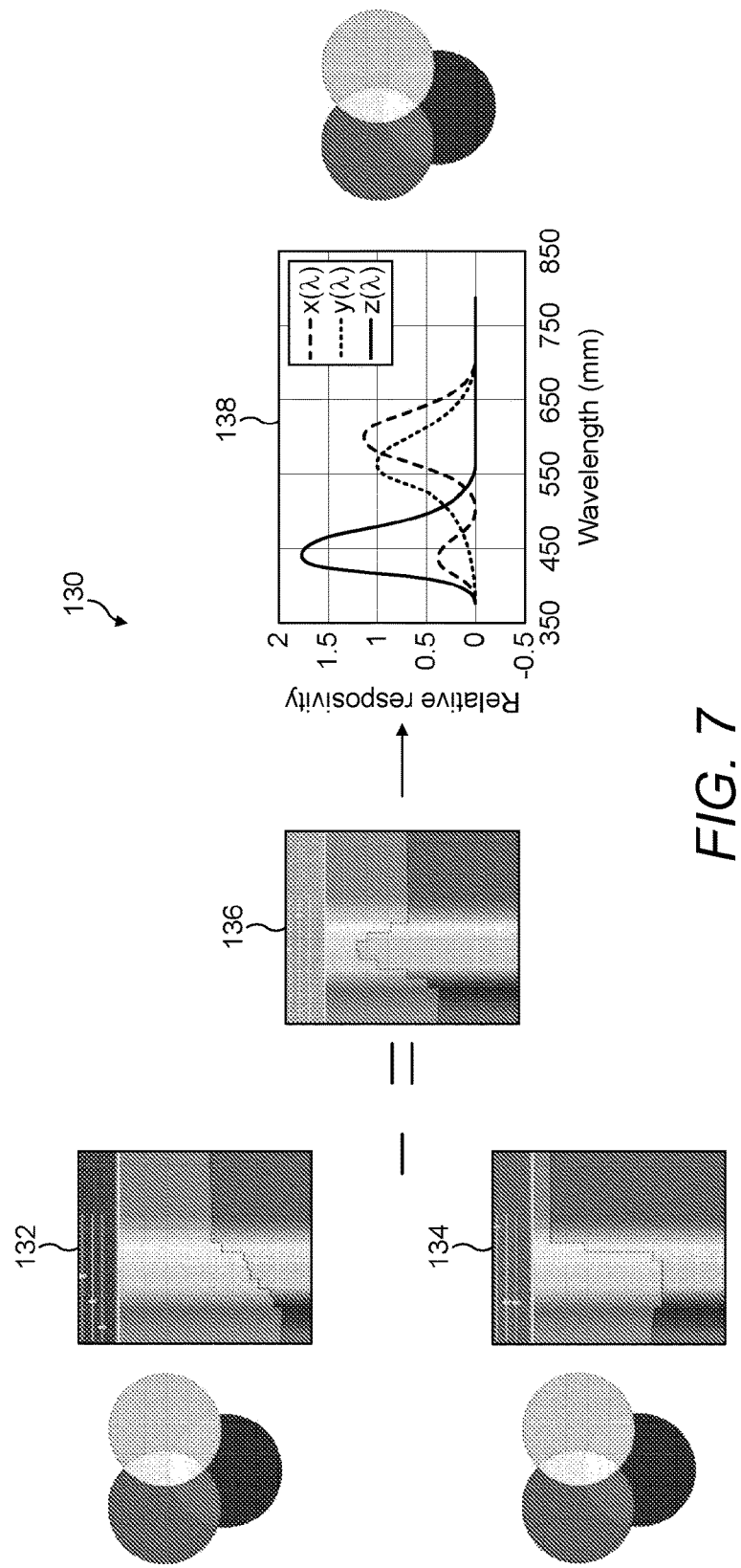
FIG. 7 is a schematic representation of a colour de-blending technique.

In order to improve the likelihood of successfully determining that staining of a kernel patch of the captured digital image, which represents the introduced note, is due to a staining ink, it is necessary to take into account colour changes that may occur when a staining ink blends with colours that are present on the introduced note. A colour de-blending technique may therefore be used, as will now be described with reference to FIG. 7.

The de-blending technique operates on the basis that dyes are additive in nature, by estimating the cause of changes in the reflectance of the introduced note over different wavelengths. The de-blending technique makes use of a piecewise constant spectrum allowing additive colours to be blending on a wavelength level.

The kernel patch of the captured digital image and the corresponding kernel patch of the reference image each have a colour value, which can be expressed as an RGB (red, green, blue) triplet value. As with the phenomenon of metamerism, many different spectra can create the same RGB triplet value. Thus, a first step of the colour de-blending technique is to convert the colour value of the kernel patch of the captured digital image and the colour value of the corresponding kernel patch of the reference image into respective best guess spectra, as shown at 132 and 134 in FIG. 7. Each best guess spectrum consists of 21 values between 361.8 nm and 794.8 nm that could reasonably form the source RGB triplet (i.e. the colour value of the kernel patch of the captured digital image and the colour value of the corresponding kernel patch of the reference image).

A reasonable spectrum is formed by attempting to minimise the variation between wavelengths as much as possible. Due to conversion linearity it is possible to construct spectra for red, green, blue, cyan, magenta, yellow and white, which can be combined using as much white as possible followed by secondary colours and finally primary colours if needed.

An addition colour spectrum 136 can be formed by dividing the colour spectrum 134 of the kernel patch of the reference image by the colour spectrum 132 of the corresponding kernel patch of the captured digital image on a per spectrum basis. The resulting addition colour spectrum can be converted back into an RGB triplet using CIE colour matching tables 138 via the XYZ colour space, and this RGB triplet can be compared to known dyes to generate the dye hue similarity metric 110 which is used as described above to determine whether staining that appears in the kernel patch of the captured digital image is due to the presence of a staining dye on the introduced note.

The process used in stage 50, in which global spatial information of the stain is used to increase the accuracy with which the area of staining detected is calculated, will now be described with reference to FIG. 8, which is a flow diagram illustrating steps used in the process 50.

Once all of the kernel patches of the captured digital image have been compared to the corresponding kernel patches of the reference image as described above, the overall spatial information of any detected stain is used to detect further staining that was not initially classified as such. This process involves making a second assessment of each of the kernel patches of the captured digital image using information that was calculated and stored during the initial assessment of those kernel patches.

Thus, at step 152 a kernel patch of the captured digital image to be tested is identified, and kernel patches neighbouring the identified kernel patch are also identified. The information generated and stored for each of the neighbouring kernel patches during the initial assessment of those neighbouring kernel patches is examined to determine if any of those neighbouring patches was deemed to be stained in the initial assessment. If so, the kernel probability score of the kernel patch being tested is increased (step 156). This increase in the kernel probability score of the kernel patch being tested may be based on the number of neighbouring kernel patches that were previously deemed to be stained. For example, if only one neighbouring kernel patch is deemed to be stained, the kernel probability score of the kernel patch being tested may be incremented by one, whereas if two neighbouring kernel patches are deemed to be stained the kernel probability score of the kernel patch being tested may be increased by two, and so on.

On the other hand, if none of the kernel patches neighbouring the kernel patch being tested has previous been deemed to be stained, the kernel probability score of the kernel patch being tested may be decreased (step 158).

Once all of the kernel patches of the captured digital image have been tested in this way, the total extent of the staining can be quantified based on the number of kernel patches having a kernel probability score that meets a pre-determined threshold.

If the total extent of the staining meets a threshold a decision is made to retain the introduced note without providing the requested goods or services, and so the processing system 18 causes the payment machine 10 to retain the note without providing the requested goods or services. On the other hand, if the extent of the staining does not meet the threshold the note is accepted, and the processing system 18 causes the payment machine 10 to retain the note and provide the requested goods or services.

It will be appreciated that the spatial adjustment process used at step 50 is an optional step that increases the accuracy with which the extent of staining of a bank note or other media item can be determined. This step could be omitted if required, such that the extent of any staining is determined by comparing the number of kernel patches of the captured digital image that are deemed to be stained on an initial assessment, based on the kernel probability score calculated for each kernel patch at step 30, to the threshold.

To add in apprehending and prosecuting thieves, the machine 10 may be provided with an outwardly facing camera or other imaging device, and the processing system 18 may be configured to actuate the camera if the total extent of staining of an introduced bank note meets the threshold, such that an image of the user of the machine 10, e.g. an image of the user's face, is captured. This image could be stored by the machine 10 and shared with other automated payment machines, and compared with other stored images to identify multiple instances of the same user attempting to use stained notes. If multiple instances of the same user attempting to use stained notes are identified in this way, the images of this user may be shared with law enforcement authorities. Alternatively, the machine 10 may share the captured image of the user with law enforcement authorities as soon as it is captured.

Although the invention has been described above using the example of an automated payment machine that is configured to detect staining of bank notes, it will be appreciated that the method and apparatus described above is equally suitable for detecting staining, damage or degradation of other media items, for example tickets or the like.

What is claimed is:

1. A method for detecting staining on a media item, the method comprising:
    capturing a digital image of the media item, the digital image comprising a plurality of pixels representing colour information of the media item;
    comparing the captured digital image to a reference image, wherein comparing the captured digital image to the reference image comprises:
    determining the nature of the media item;
    retrieving a corresponding reference image from a database;
    generating a histogram for each of a plurality of kernel patches of the captured digital image, wherein each of the plurality of kernel patches of the captured digital image covers an area of the captured digital image, such that the entire captured digital image is covered by the plurality of kernel patches;

comparing the histogram for each of the plurality of kernel patches of the captured digital image to a histogram of a corresponding kernel patch of the reference image to generate a distance metric; and based on the generated distance metrics, determining if staining is present on the media item.

2. A method according to claim 1 wherein the generated distance metric is a Chi Square distance between the histogram of the kernel of the captured digital image and the histogram of the corresponding kernel of the reference image.

3. A method according to claim 1 wherein pixels of the kernels are weighted according to a Gaussian distribution applied over a colour distance of the pixels and histogram intervals to which the pixels are to be added.

4. A method according to claim 1, wherein each of the plurality of kernel patches overlaps a neighbouring kernel patch.

5. A method according to claim 1, further comprising applying a transformation to the captured digital image to align and resize the captured digital image to correspond in size and orientation to the reference image.

6. A method according to claim 1, wherein capturing the digital image of the media item comprises capturing a digital image of one or both sides of the media item.

7. A method according to claim 1 wherein the media item is a bank note.

8. A method according to claim 1 wherein the reference image is retrieved from a database containing a plurality of reference images.

9. A method according to claim 1, further comprising, for each individual kernel patch of the plurality of kernel patches of the captured digital image:

identifying kernel patches neighbouring the individual kernel patch;

examining each neighbouring kernel patch to assess whether that neighbouring kernel patch is deemed to be stained;

if a neighbouring kernel patch is deemed to be stained, increasing a kernel probability score of the individual kernel patch;

quantifying the extent of staining by comparing the number of individual kernel patches of the captured digital image that have a kernel probability score that meets a threshold.

10. A method according to claim 9 further comprising:

if no neighbouring kernel patch is deemed to be stained, decreasing a kernel probability score of the individual kernel.

11. A method according to claim 1 wherein pixels of the kernels are weighted such that pixels positioned towards a centre of the kernel have higher weights than pixels positioned towards edges of the kernel.

12. A method according to claim 11 wherein the pixels of the kernels are weighted according to a two-dimensional spatial Gaussian distribution.

13. A system for detecting staining on a media item, the system comprising:

an imaging device for generating digital image of the media item, the digital image comprising a plurality of pixels representing colour information of the media item; and a processor, the processor being configured to perform the method claim 1.

14. A system according to claim 13, wherein the system further comprises a camera for capturing an image of a user of the system, and wherein the processor is configured to actuate the camera to capture an image of the user if the total extent of staining on the media item meets a threshold.

15. A method according to claim 1 further comprising determining the nature of detected staining based on the generated distance metrics.

16. A method according to claim 15 wherein determining the nature of the detected staining comprises, for each kernel patch of the captured digital image:

generating a dye certainty metric for the kernel patch; and combining the generated dye certainty metric with the generated distance metric for the kernel patch to generate a kernel probability score which is representative of the likelihood that the detected staining is due to a staining dye.

17. A method according to claim 16 wherein the dye certainty metric is weighted by a hue certainty metric.

18. A method according to claim 17 wherein the hue certainty metric depends upon saturation and intensity values of the kernel patch.

19. A method according to claim 16 wherein the dye certainty metric is weighted by an intensity difference metric.

20. A method according to claim 19 wherein the intensity difference metric is generated by comparing an intensity value of the kernel patch of the captured digital image with an intensity value of a corresponding kernel patch of the reference image.

21. A method according to claim 16 wherein the dye certainty metric is weighted by a dye hue similarity metric.

22. A method according to claim 21 wherein the dye hue similarity metric is generated by comparing a hue value of the kernel patch of the captured digital image with a hue value of a known staining dye.

23. A method according to claim 22 wherein the dye hue similarity metric is generated by performing a colour de-blending process using colour values of the kernel of the captured digital image and the corresponding kernel of the reference image.

24. A method according to claim 23 wherein the colour de-blending process comprises:

generating, from the colour values of the kernel of the captured digital image and the corresponding kernel of the reference image, respective captured and reference colour spectra;

dividing the reference colour spectrum by the captured colour spectrum to generate an addition colour spectrum;

converting the addition colour spectrum to an RGB triplet; and comparing the RGB triplet to a known dye to generate the dye hue similarity metric.

* * * * *